United States Patent [19]

Beatty et al.

[11] Patent Number: 4,921,690

[45] Date of Patent: May 1, 1990

[54] METHOD OF ENHANCING THE BIODISTRIBUTION OF ANTIBODY FOR LOCALIZATION IN LESIONS

[75] Inventors: John D. Beatty; Barbara G. Beatty, both of Arcadia, Calif.; Rosemary B. Duda, Chicago, Ill.

[73] Assignee: City of Hope, Duarte, Calif.

[21] Appl. No.: 180,447

[22] Filed: Apr. 12, 1988

Related U.S. Application Data

[63] Continuation-in-part of Ser. No. 946,950, Dec. 29, 1986, abandoned.

[51] Int. Cl.$^5$ .................... A61K 49/02; A61K 39/395
[52] U.S. Cl. ........................................ 424/1.1; 424/9; 424/85.91; 530/402
[58] Field of Search .................... 424/1.1, 9, 85.91; 530/402

[56] References Cited

U.S. PATENT DOCUMENTS

| | | | |
|---|---|---|---|
| 4,565,687 | 1/1986 | Khazaeli et al. | 424/1.1 |
| 4,624,846 | 11/1986 | Goldenberg | 424/1.1 |
| 4,665,897 | 5/1987 | Lemelson | 424/1.1 X |

*Primary Examiner*—John S. Maples
*Attorney, Agent, or Firm*—Edward S. Irons

[57] ABSTRACT

A method for enhancing the biodistribution of antibody for localization in lesions comprising initially exposing a mammalian subject containing lesion-associated marker substance to a first antibody specific for a given epitope of the marker substance, and after a period of time such that the marker substance has associated with the antibody, exposing the mammal to a further amount of the same antibody, or a second antibody specific either for an epitope of the marker substance different from the epitope for which the first antibody is specific, or for the same epitope of the marker substance as the first antibody but of a different binding affinity from the first antibody.

17 Claims, 6 Drawing Sheets

METHOD OF ENHANCING THE BIODISTRIBUTION OF ANTIBODY FOR LOCALIZATION IN LESIONS

This application is a continuation-in-part application of Ser. No. 946,950 filed Dec. 29, 1986 now abandoned.

BACKGROUND OF THE INVENTION

This invention relates to methods of enhancing the biodistribution in a mammalian subject. More specifically this invention relates to the use of monoclonal antibodies for localization, detection, and treatment of lesions, including tumors, in humans.

The diagnostic and therapeutic use of radioactively labeled antibodies specific to substances produced by or associated with tumors to detect or locate tumors is recognized.

Carcinoembryonic antigen (CEA) is an example of an antigen or marker substance produced by tumor cells and associated with tumor cell membrane. Some of the CEA becomes separated from the tumor cell and progresses through the interstitial fluid and eventually reaches the circulation of the host.

Administration of antibody specific for CEA to a human or animal with a CEA-producing tumor results primarily in the antibody attaching to the CEA in circulation while some reaches the tumor site which contains the highest amount of antigen. Eventually if a steady state equilibrium can be reached, antibody will accumulate at the tumor.

U.S. Pat. No. 3,927,193 to Hansen et al. describes a method for determining the site of tumors which produce or are associated with CEA using labeled antibodies to CEA. U.S. Pat. No. 4,311,688 to Burchiel et al. describes the detection of cells that produce human chorionic gonadotropin (hCG) and compounds similar to the beta-chain of hCG by first administering anti-hCG or anti-hCG-beta and then administering radioactively labeled antibodies to anti-hCG-beta or anti-hCG. U.S. Pat. No. 4,331,647 to Goldenberg describes both the detection of tumors using mixtures of radiolabeled antibody fragments specific to tumor-associated markers and tumor radiotherapy using antibody fragments labeled with radiotherapeutically effective radioisotopes. U.S. Pat. No. 4,478,815 to Burchiel et al. likewise describes the use of radio-labeled antibody fragments to detect tumors producing hCG or other tumor associated antigen.

A major problem encountered in the use of radiolabeled antibodies to detect or treat tumors is the uptake or accumulation of radioactivity caused by radiolabeled antibodies, antibody fragments, or their metabolites in the blood pool, in interstitial fluids, or other tissues such as the liver and spleen. The isotopes most frequently chosen for radioimaging are the iodine isotopes (I-123, I-125, and I-131) and indium-111. While indium-111 has several advantages over the most commonly used iodine isotope, I-131, the use of indium-111 as a label for monoclonal or other antibodies has the disadvantage of a marked uptake in normal liver.

If administered antibody is radiolabeled and there is a substantial amount of marker substance such as CEA available in the circulation, then antibody-antigen complexes formed will be cleared rapidly, primarily by the liver and spleen. Such uptake of radioactivity in these organs, especially the liver, predominates over any uptake by tumor and significantly reduces the resolution of tumor localization using radiolabeled antibodies. The amount of labeled antibody in the blood will drop rapidly due primarily to liver uptake and the ratio of uptake in liver as compared to that of the blood (L/B ratio) is very high. The detection or localization of lesions located in or near the liver is consequently particularly difficult because of the increased uptake of radiolabeled substances.

In an effort to solve the general problem of accumulated radioactivity in the body, U.S. Pat. No. 4,348,376 to Goldenberg, describes the localization of tumors associated with CEA by concurrently administering both a radiolabeled antibody specific to CEA, and a background compensating material, normal immunoglobulin from the same or different species as that used to prepare the antibody, which is radiolabeled with a different radioisotope of the same element used to label the antibody to CEA. The level of radioactivity of the labeled normal immunoglobulin is used to determine the distribution of background radioactivity due to non-targeted specific antibody, which background distribution is then subtracted from the total activity. U.S. Pat. No. 4,444,744 to Goldenberg similarly describes a method for detecting other tumor-associated antigens.

U.S. Pat. No. 4,460,561 to Goldenberg describes a method of tumor therapy wherein thermal neutrons excite a boron-10 isotope-containing antibody which has been localized by detection of an attached radioisotope label.

A further method of diminishing nontumor-associated antibody is described in Goldenberg, PCT Pat. No. WO9500522. A radiolabeled tumor-specific antibody is injected into the subject, and at a time after injection of the antibody sufficient to permit maximum selective uptake thereof by the tumor, a second, nonradiolabeled antibody specific against the first radiolabeled antibody is injected. The second antibody binds with an amount of labeled antibody not associated with tumor tissue such that the level of circulating (nontumor-associated) radiolabeled antibody is decreased. The mechanism of liver uptake of indium-labeled antibodies is not yet known. Accumulation of indium-111 in liver tissue is seen in both tumor and non-tumor bearing mice. However, tumor bearing mice have significantly higher liver levels of radioactivity, up to 40–50% injected dose/gram (ID/g), than non-tumor bearing mice, 6–10% ID/g. In the nude mice model, the size of the tumor directly affects the liver uptake of indium-111 and inversely affects tumor uptake of indium-111. Williams, L. E., et al., *J. Nucl. Med.* 29:103–109 (1988); Hagan, P. L., et al., *J. Nucl. Med.* 24:422–427 (1986); Philben, V. J., et al., *Cancer* 57:571–576 (1986); Pedley, R. B., et al., *Eur. J. Nucl. Med.* 13:197–202 (1987).

In the following description of the present invention, the term "biodistribution" refers to the distribution of antibody in a subject to which antibody has been administered. By contrast, "uptake" refers to the quantity of antibody in a given tissue. The terms "lesion-associated marker substance", "marker substance", or "marker" refers to a substance produced by or associated with a lesion and for which an administered antibody is specific. A lesion is an abnormal change in the structure of an organ or part due to injury or disease, e.g., a tumor.

SUMMARY OF THE INVENTION

In general, the invention features a method for enhancing the biodistribution of antibody for localization in lesions comprising initially exposing a mammalian subject containing a lesion-associated marker substance to a first antibody specific for a given epitope of the marker substance, and after a period of time such that the marker substance has associated with the antibody, exposing the mammal to a further amount of the same antibody, or a second antibody specific either for an epitope of the marker substance different from the epitope for which the first antibody is specific or for the same epitope of the marker substance as the first antibody but of a different binding affinity from the first antibody.

In one preferred embodiment, the subsequently administered antibody is labeled with an agent detectable by radioimaging, photoimaging, or other suitable means. Imaging of lesion-associated marker is enhanced due to reduced uptake of the subsequently administered antibody by liver and spleen tissue.

In the other preferred embodiment, the subsequently administered antibody is labeled with a therapeutically effective agent. The therapeutic effects of this agent with respect to the lesion are enhanced due to reduced uptake of the therapeutic-labeled antibody by non-lesion tissue.

Other features and advantages of the invention will be apparent from the following description of the preferred embodiments, and from the claims.

DETAILED DESCRIPTION

Figure 1:
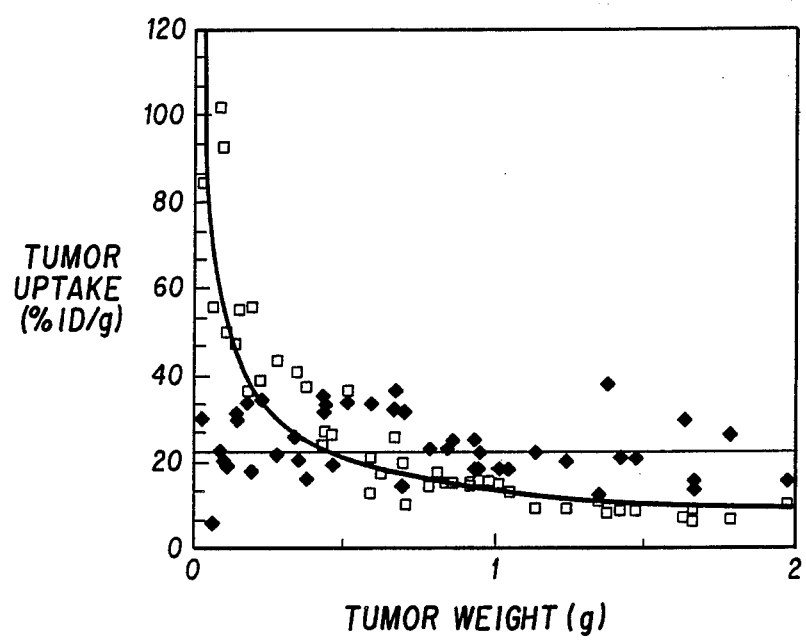
FIG. 1 is a graph showing tumor uptake of T84.66 monoclonal antibody (MAB) labeled with $^{111}$In as a function of tumor weight in specific MAB pretreated (0.2 mg T84.66) (◆) and non-treated phosphate buffered saline (PBS) (□) mice.

Methods have been discovered for enhancing the biodistribution of antibody specific for a lesion-associated marker in a mammalian subject. A mammalian subject containing a marker substance produced by or associated with a lesion is pretreated with an unlabeled antibody specific for the marker substance. At a time after the initial exposure such that the antibody complexes with circulating marker substance or with marker substance in normal tissue such as the liver, the subject is again exposed to the same antibody or an antibody specific for the same or different epitope of the marker substance. It is also possible to increase biodistribution by combining the pretreatment and treatment steps so as to administer unlabeled and labeled antibody simultaneously. Exposure to the antibody may be accomplished by, for example, intravenous, intraperitoneal, parenteral or subcutaneous injection or oral administration.

The first exposure of the subject to the antibody causes the subject to recognize the antibody or to change its response to subsequently administered antibody which results in an enhanced biodistribution of that antibody upon the subject's subsequent reexposure to it. Specifically, the first exposure to a given antibody causes a decrease in the uptake of the subsequently administered labeled or unlabeled antibody by tissues such as the liver and spleen. This allows more of the subsequently administered antibody to remain in the blood and eventually reach the lesion sites.

The decreased uptake of antibody by the liver and spleen which is consequent from the methods of this invention is useful in a variety of contexts, for example, lesion detection and location in humans. In particular, lesions situated in or near the human liver and spleen are more easily detected and located due to the reduced uptake of labeled antibody by those tissues. Imaging tumors in or near the liver is of particular importance with respect to colon cancer since colon cancer metastases are frequently found in or near the liver.

A human subject in which the presence and/or location of a lesion is to be ascertained by imaging means is first exposed to an antibody specific for a given lesion-associated marker. After one or a number of exposures, and after a period of time such that the subject has come to recognize the antibody such that circulating marker substance complexes with the antibody, the subject is exposed to the same broad antibody which is labeled with a detectable agent. This label could be a radionuclide such as indium-111 or technecium-99m suitable for gamma imaging, or could be a magnetic contrast agent such as gadolinium, manganese, or iron for magnetic resonance imaging. By subsequently photoscanning or employing other suitable methods for detecting the site or sites of label accumulation, the presence and/or location of lesions may be determined.

Application of the methods of this invention is also useful for providing a highly specific lesion therapy. A human or animal subject having a lesion with which is associated a marker substance is first exposed to an antibody specific for that marker. After a period of time such that the subject has come to recognize that antibody, the subject is exposed to the same antibody which is labeled with a therapeutically effective agent such as yttrium-90 or methotrexate. The recognition induced in the subject by prior exposure to the antibody leads to reduced association of the labeled antibody with non-lesion tissue and concomitantly, increased association with lesion-associated marker substance. Thus, the destructive effects of the therapeutically effective agent against lesion cells are enhanced.

In general the antibodies used to practice this invention are monoclonal antibodies (MABs) of mammalian origin synthesized by known genetic engineering or synthesized in vitro or in vivo. Chimeric antibodies comprising murine variable regions and human constant regions are also useful.

The following example broadly illustrates the enhanced biodistribution of a given labeled antibody caused by prior exposure of the subjects to the same antibody in unlabeled form to which they are subsequently exposed. Specifically, it illustrates the phenomenon of recognition by which specific organs in a subject, exposed to a given antibody, by some means identify, recognize, or change their response to the antibody upon a later exposure to it. The uptake of the labeled antibody is greatly reduced due to the prior exposure to the unlabeled antibody.

The example also illustrates, when compared to the further examples set forth, the effect of tumor size on the practice of the present invention.

EXAMPLE 1

Nude female BALB/c mice were injected with approximately $1 \times 10^6$ cells of the CEA-producing human colon cancer-derived cell line LS174T subcutaneously (sc) on day zero. Tumors were palpable on day seven.

The mice were divided into five groups. To the first group, a control, phosphate buffered saline (PBS) was administered. Different monoclonal antibody pretreatment regimes were administered to the other four groups of mice. For the initial exposure step (or pretreatment), PBS or one of the three types of MAB were used. All three MABs were specific for CEA.

The mice were administered either the PBS control or anti-CEA MABs intraperitoneally on days 7, 8, 9 and 10. The total MAB pretreatment dose of 2.5 mg was given as 1.0, 0.5, 0.5 and 0.5 mg on those successive days. The MAB pretreatment dose of 0.25 mg was given at one-tenth these doses on those successive days. All five groups of mice were injected with 2.5 micrograms T84.66 MAB labeled with 12.5 $\mu$Ci of indium-111 on day 13. On day 15, randomly selected animals from each group were imaged by photoscintigraph. On day 16, the biodistributions of labeled T84.66 were determined.

One of the monoclonal antibodies used for pretreatment, T84.66, is the same, except for the absence of a label, as that to which all five groups of mice were subsequently exposed in the second step. T84.66, an IgG$_1$ MAB, and T84.12, an IgG$_{2a}$ MAB, recognize the same epitope on CEA as described by Wagener, C., et al., *J. Immunol.* 103:2303–2307 (1983). The ZCE025 MAB, an IgG$_1$ MAB, is specific for a different epitope on CEA and was obtained from Hybritech, Inc., San Diego, Calif.

The MABs were conjugated to DTPA using the method of Paxton, R. J., et al., *Cancer Research* 45:5694–5699 (1985) and labeled with indium-111 at a ratio of 5 $\mu$Ci/$\mu$g antibody. The $^{111}$In-labeled anti-CEA MAB is also referred to below as "Indacea".

Table I shows the results of the pretreatments. In the following table "n" denotes the number of mice in each of the five groups.

TABLE I

MURINE BIODISTRIBUTION OF LS174T SUBCUTANEOUS XENOGRAPHS-THE EFFECT OF ANTIBODY EXPOSURE PRIOR TO ADMINISTRATION OF INDIUM-111 LABELED T84.66 (MEAN ± SE)

| Pretreatment Substance | Saline | T84.12 | Phosphate Buffered ZCE025 | T84.66 | T84.66 |
|---|---|---|---|---|---|
| Pretreatment Dose (mg) | — | 2.5 mg | 2.5 mg | 2.5 mg | 0.25 mg |
| n | 10 | 9 | 8 | 9 | 6 |
| Indium Labeled T84.66 | 2.5 ug | 2.5 ug | 2.5 ug | 2.5 ug | 2.5 ug |
| (a) % ID/g ± SE* | | | | | |
| Blood (B) | 5.95 ± 1.79 | 4.03 ± 1.29 | 2.27 ± 0.75 | 13.57 ± 1.17 | 10.28 ± 1.50 |
| Liver (L) | 24.69 ± 4.43 | 24.31 ± 2.81 | 29.63 ± 2.77 | 8.35 ± 1.21 | 8.12 ± 0.60 |
| Spleen | 16.88 ± 2.93 | 9.40 ± 1.40 | 14.62 ± 0.88 | 7.25 ± 0.70 | 6.28 ± 0.52 |
| Kidney | 11.96 ± 4.31 | 8.40 ± 0.79 | 6.46 ± 0.65 | 12.81 ± 1.26 | 11.51 ± 0.83 |
| Lung | 3.81 ± 1.02 | 3.04 ± 1.08 | 1.83 ± 0.40 | 8.16 ± 1.07 | 5.58 ± 0.82 |
| Tumor (T) | 38.67 ± 10.49 | 24.15 ± 7.18 | 17.65 ± 3.96 | 10.89 ± 0.68 | 22.86 ± 2.04 |
| (b) % ID/organ ± SE** | | | | | |
| Blood | 9.63 ± 2.97 | 6.21 ± 1.95 | 3.55 ± 1.21 | 20.90 ± 1.91 | 16.35 ± 2.20 |
| Liver | 23.71 ± 3.73 | 24.01 ± 2.51 | 29.70 ± 2.22 | 8.23 ± 1.34 | 8.40 ± 0.86 |
| Tumor | 8.80 ± 1.46 | 15.95 ± 1.42 | 11.44 ± 1.85 | 6.99 ± 1.71 | 9.68 ± 2.38 |
| (c) Ratios ± SE*** | | | | | |
| (T/L) | 3.59 ± 1.43 | 1.56 ± 0.69 | 0.72 ± 0.21 | 1.42 ± 0.11 | 2.90 ± 0.33 |
| (T/B) | 8.20 ± 1.04 | 6.36 ± 0.45 | 9.72 ± 1.30 | 0.82 ± 0.32 | 2.59 ± 0.57 |
| (L/B) | 14.53 ± 4.33 | 12.75 ± 3.03 | 25.96 ± 6.52 | 0.63 ± 0.09 | 1.05 ± 0.39 |
| (d) Tumor Wt (g) ± SE | 0.57 ± 0.17 | 1.14 ± 0.23 | 0.82 ± 0.13 | 0.78 ± 0.2 | 0.48 ± 0.13 |

*% ID/g, percent injected dose per gram of tissues.
**% ID/organ, percent injected dose per organ.
***ratio of % ID/g for two different tissues.

The first column of Table I shows that the administration of PBS control followed by administration of indium-labeled T84.66 resulted in the greatest uptake in both tumor and liver (% ID/g). In keeping with this, the scintiscan image had shown localization of intensity primarily in the tumor and the liver. The ratios of uptake as measured by the percentage of the injected dose of MAB per gram of tissue for different tissues for the PBS control are 3.6 and 8.2 for tumor to liver (T/L) and tumor to blood (T/B), respectively. The liver to blood ratio (L/B) was much higher at 14.5. The last column of Table I shows that prior administration of 0.25 mg of T84.66 followed by administration of indium-labeled T84.66 resulted in the greatest uptake in tumor alone. In keeping with this, the scintiscan images had shown localization of intensity in the tumor alone. The ratios of uptake shown in Table I for the 0.25 mg T84.66 pretreatment were 2.9 and 2.6 for tumor to liver and tumor to blood, respectively. However, the liver to blood ratio was very low at 1.1.

The higher dose of T84.66 used for initial exposure (2.5 mg) resulted in lower liver uptake, but also lower uptake in the tumor. This resulted in all tissue ratios being near unity (1). This data shows that prior administration of T84.66 results not only in decreased accumulation of labeled T84.66 antibody in the liver, but also in increased retention of labeled T84.66 in the blood. Such retention in the blood is consistent with decreased accumulation in the liver. Moreover, such accumulation in the blood is consistent with increased tumor uptake, since, in contrast to antibody taken up by the liver, antibody in the blood may eventually become associated with the marker substance for which it is specific.

While the above example also appears to show that prior administration of an antibody similar, but not identical, to the subsequently administered antibody does not cause an enhanced biodistribution of the subsequently administered antibody, this data is anomolous, in view of the following examples, due to the fact that the tumor sizes in the host animals varied by large amounts (about 0.006 g to about 1.76 g). The data for the PBS control column in Table I, for example, included three mice with tumors less than 0.1 g (0.006 g, 0.060 g, 0.068 g) which resulted in mean tumor uptake of 80.74±11.01% ID/g and high T/L ratios. That the tumor uptake and T/L ratios were much higher than would be expected for an average tumor size of 0.57 g (average tumor size for PBS column of Table I) is explained by reference to FIGS. 1 and 2.

Figure 2:
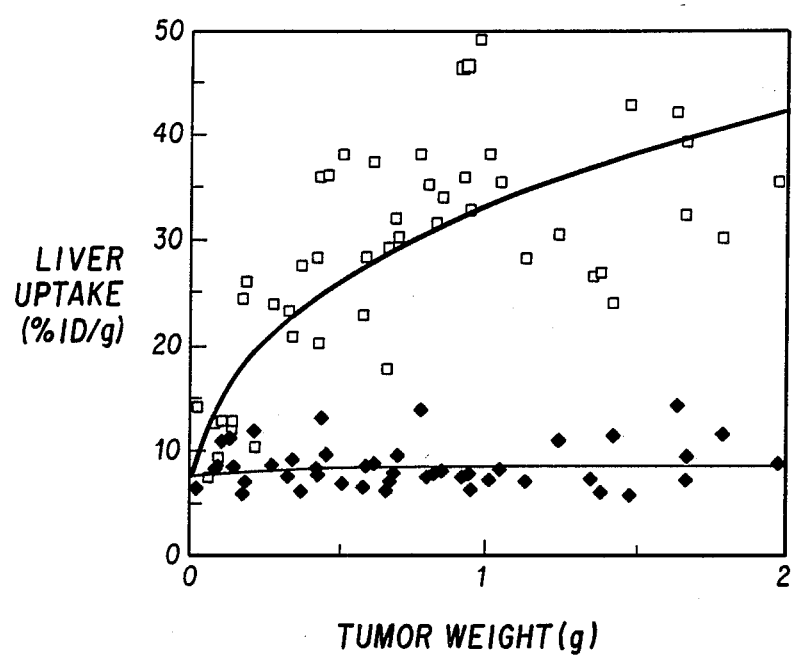
FIG. 2 is a graph showing liver uptake as a function of tumor weight in specific MAB pretreated (0.2 mg T84.66) (◆) and non-treated (PBS) (□) mice.

FIGS. 1 and 2 show that tumor uptake of Indacea in control mice has an inverse logarithmic relationship with tumor size, whereas liver uptake has a direct logarithmic relationship with tumor size. These data were obtained from 46 PBS control animals compiled from several different experiments. The most rapid rate of decrease in % ID/g tumor with increase in tumor size was seen for very small (<0.5 g) tumors (FIG. 1). For larger tumors (>0.5 g), the decrease in % ID/g tumor with increase in tumor size was not as marked. Similarly, the rate of increase in liver uptake (% ID/g) was higher for tumors between 0.01 and 0.5 g than for larger tumors between 0.5 and 1.5 g (FIG. 2). Liver uptake (% ID/g) in animals with tumors of approximately 1 g or more ranged between 30-50%. This value was twice that found in animals with tumors of less than 0.5 g (15-25%). In order to further examine the effect of MAB pretreatment on the tissue biodistribution of Indacea it was therefore essential to keep the tumor size consistent within an experiment.

The effect of pretreating tumor bearing mice with 100 fold excess of unlabeled T84.66 MAB (0.2 mg) on tumor and liver uptake of Indacea (2 μg) is also shown in FIGS. 1 and 2 respectively. It can be seen that with this dose of MAB pretreatment, the amount of radiolabel associated with the tumor and the liver was independent of tumor mass over the size range studied. Liver uptake of Indacea was reduced to an average value of 8.43±0.30 % ID/g irrespective of the tumor size. This value was very similar to that seen in non-tumor bearing mice as reported by Jakowatz, J. G., et al., *Cancer Research* 45:5700–5706 (1985). Similarly, the average tumor uptake of radiolabel with pretreatment was very uniform (23.7±1.04 % ID/g) and independent of tumor size. As shown in FIG. 1, specific antibody pretreatment resulted in an inhibitory effect on tumor uptake of Indacea by tumors smaller than 0.5 g. On the other hand, tumors larger than 0.5 g showed significant enhancement of tumor uptake with MAB pretreatment (p<0.0005).

The following example shows the effects of various MAB pretreatment doses on biodistribution.

EXAMPLE 2

Table II shows the effect of changing the dose of T84.66 pretreatment MAB on the tissue biodistribution of 2.0 μg of (10 μCi) T84.66 Indacea in a series of 10-fold dilutions from 2.0 mg to 0.002 mg in mice bearing sc tumors.

TABLE II

EFFECT OF DOSE OF SPECIFIC MAB PRETREATMENT ON BIODISTRIBUTION OF INDACEA IN NUDE MICE BEARING SUBCUTANEOUS LS174T XENOGRAFTS

| Pretreatment Dose (mg) | 2.0 | 0.2 | 0.02 | 0.002 | PBS |
|---|---|---|---|---|---|
| Tissue Uptake (% ID/g ± SE) | | | | | |
| Blood (B) | 11.89 ± .82 | 10.62 ± .89 | 3.42 ± .66 | 2.03 ± .37 | 2.71 ± 0.39 |
| Liver (L) | 7.94 ± .43 | 8.87 ± .47[a] | 26.51 ± 2.76 | 28.78 ± 1.38 | 33.76 ± 1.51[a] |
| Tumor (T) | 12.44 ± .44[b] | 21.47 ± 1.11 | 26.87 ± 3.54 | 18.56 ± 1.57 | 15.85 ± 1.25[b] |
| Tissue Ratios (±SE) | | | | | |
| T/L | 1.61 ± .09 | 2.19 ± .13[c] | 1.22 ± .33 | 0.68 ± .07 | 0.47 ± 0.05[c] |
| T/B | 1.10 ± .10 | 2.83 ± .48 | 9.52 ± 1.28 | 11.61 ± 1.19 | 7.5 ± 0.60 |
| L/B | 0.76 ± .13 | 1.13 ± .18 | 13.20 ± 4.28 | 22.16 ± 3.84 | 21.13 ± 3.25 |
| Tumor Weight | | | | | |
| (g ± SE) | 0.81 ± .07 | 0.71 ± .04 | 0.72 ± .08 | 0.84 ± .09 | 0.92 ± .06 |
| Number of Mice | | | | | |
| (n) | 13 | 22 | 8 | 13 | 25 |

[a,c] = p < 0.0005
[b] = p < 0.01

In the experiments represented in Table II mice were injected sc with $1 \times 10^6$ LS174T cells on day 0, and on day 7 received either 2.0, 0.2, 0.02, 0.002, or 0 mg of T84.66 intraperitoneally (ip) over a period of 3 days. 1.0 mg MAB was administered on the first day and 0.5 mg was administered on the next 2 days. On day 14, each animal received 2 μg (10 μCi) Indacea (T84.66) ip. Nuclear scintiscans were obtained using a Siemens Pho-Gamma V camera 48 hours later. The animals were euthanized and tissue biodistributions were performed 48 hours after Indacea injection and the radiolabel uptake expressed as mean percentage injected dose per gram (% ID/g) for each tissue. The Table II results are the mean for each experiment±standard error (SE). Mean tumor weight in grams g±SE is shown as well as the number of mice (n).

Based upon the logarithmic changes in tumor and liver uptake with changes in tumor size, tumors weighing 0.5–1.5 g were selected for these studies.

As seen in Table II, at the highest dose tested (2.0 mg/mouse) the liver uptake of radiolabel was lowered substantially, but there was also a decrease in tumor accumulation (% ID/g) of the radiolabeled MAB and a rise in the blood pool radioactivity. Decreasing the dose of unlabeled MAB resulted in a lower level of Indacea in the blood, and an increase in the liver and tumor uptake of radiolabel. The radioactivity of the blood dropped 83% and the radioactivity of the liver rose 262% when the pretreatment does of T84.66 was lowered from 2.0 mg to 0.002 mg.

48 hours later as described above. Average tumor size was 0.56±0.03 g. PBS controls were matched accordingly. The results are in Table III.

TABLE III

EFFECT OF PRETREATMENT DOSE FRACTIONATION ON BIODISTRIBUTION OF INDACEA IN NUDE MICE BEARING SUBCUTANEOUS LS174T XENOGRAFTS

| Number of Fractions | 3 | 2 | 1 | PBS Control |
|---|---|---|---|---|
| Tissue Uptake (% ID/g ± SE) | | | | |
| Blood (B) | 12.78 ± 0.62 | 13.42 ± 1.29 | 13.69 ± 0.74[a] | 3.58 ± 0.49[a] |
| Liver (L) | 7.72 ± 0.43[b] | 8.73 ± 0.77 | 9.41 ± 1.33[b] | 30.04 ± 1.59 |
| Tumor (T) | 19.82 ± 1.30[c] | 30.08 ± 1.92 | 26.13 ± 1.99 | 24.69 ± 2.47[c] |
| Tissue Ratios (±SE) | | | | |
| T/L | 2.60 ± 0.21 | 3.54 ± 0.36 | 2.93 ± 0.30 | 0.98 ± 0.18 |
| T/B | 1.56 ± 0.08 | 2.32 ± 0.28 | 1.93 ± 0.16 | 9.16 ± 0.82 |
| L/B | 0.61 ± 0.03 | 0.67 ± 0.06 | 0.70 ± 0.11 | 14.30 ± 1.96 |
| Tumor Weight (g ± SE) | 0.55 ± 0.05 | 0.52 ± 0.06 | 0.60 ± 0.11 | 0.55 ± 0.05 |
| Number of Mice (n) | 5 | 4 | 5 | 29 |

[a] = $p < 0.0005$
[b,c] = $p < 0.05$

Figure 3A:
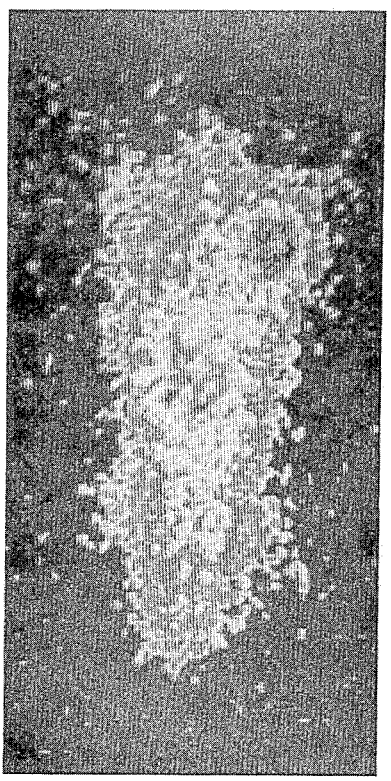
FIGS. 3a and 3b are photographs of nuclear scintiscans of mice bearing sc LS174T xenografts treated with 0.2 mg of T84.66 MAB (a) or PBS (b) 7 days prior to receiving 2 μg (10 μCi) $^{111}$In-labeled T84.66, and imaged at 48 hours.
Figure 3B:
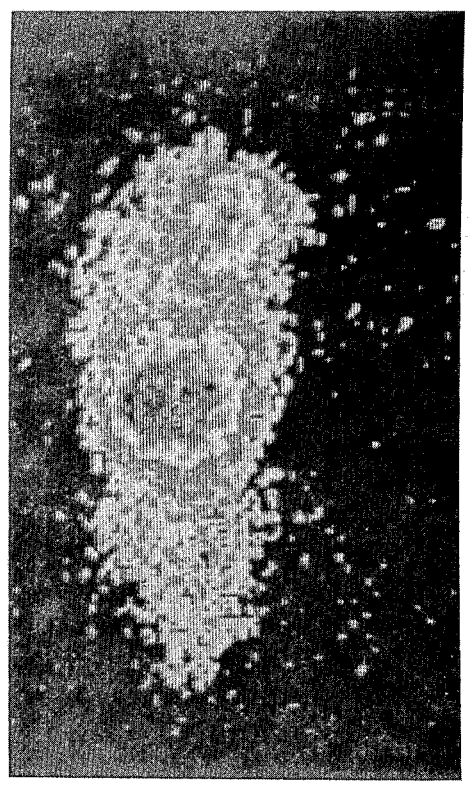

The lowest liver uptake was seen at the 2 mg and 0.2 mg doses of unlabeled T84.66, while the highest tumor uptake was seen at the 0.02 mg dose. As noted above, the 0.2 mg dose of MAB decreased the tumor uptake of $^{111}$In-MAB in tumors smaller than 0.5 g (FIG. 1). Increasing the pretreatment dose to 2.0 mg inhibited tumor uptake in tumors as large as 1.0 g. The results in Table II for tumors in the 0.5–1.5 g range show that the dose which resulted in the highest T/L ratio (2.19±0.13) and lowest L/B ratio (1.13±0.18) combination was 0.2 mg. The improvement in T/L ratios with specific antibody pretreatment was reflected in the scintiscans. FIG. 3b shows that pretreatment with 0.2 mg T84.66 was effective in decreasing the normal liver background compared to the FIG. 3a non-treated animal. This dose of MAB was used for pretreatment in the following examples which assess other MAB pretreatment parameters.

In the following example the effect of single or multiple pretreatments was ascertained.

EXAMPLE 3

Nude mice were inoculated sc with $1 \times 10^6$ LS174T tumor cells (day 0) and divided into three groups. Each group was treated ip with 0.2 mg of unlabeled T84.66 given in one dose on day 7, two doses on days 7 and 8 (0.1 mg/day) or three doses on day 7, 8 and 9 (0.1 mg on day 7, 0.05 mg on days 8 and 9). In all cases, the total cumulative pretreatment dose was 0.2 mg T84.66. In each case, 2 μg (10 μCi) Indacea (T84.66) was injected ip on day 14 and tissue biodistributions were performed As seen in Table III, the uptake of labeled MAB by the liver in all three pretreated groups was significantly lower than the liver uptake in the PBS control group ($p < 0.0005$). Concomitantly, the blood level of circulating Indacea was significantly increased in all three treated groups over that of the control ($p < 0.0005$). The tumor uptake with the unlabeled pretreatment given as three fractions was also significantly lower than in the PBS control ($p < 0.05$).

There was also a significant trend toward a lower liver uptake of radioactivity with increasing number of pretreatment administrations ($p < 0.05$). Tumor uptake of $^{111}$In-T84.66 was lower in the animals that received the treatment in three doses compared to the other treatment groups. Despite the tumor and liver uptake variations, the T/L ratios of the three treatment groups were significantly higher than the T/L ratio of the controls and did not vary significantly.

In the following example the timing of the pretreatment antibody prior to the labeled antibody was determined.

EXAMPLE 4

Nude mice were inoculated sc with $1 \times 10^6$ LS174T cells on day 0. Unlabeled T84.66 (0.2 mg) was administered ip in one dose between 20 minutes (m) and 7 days (d) prior to Indacea (T84.66). A PBS control group received no pretreatment. Indacea was injected ip (2 μg, 10 μCi) on day 14. Tissue biodistributions were performed 48 hours after Indacea injection and expressed as % ID/g±SE. Results are in Table IV.

TABLE IV

EFFECT OF TIMING OF PRETREATMENT ON BIODISTRIBUTION OF INDACEA IN NUDE MICE BEARING SUBCUTANEOUS LS174T XENOGRAFTS

| Time of Pretreatment Prior To Indacea | −20 m | −13 h | −48 h | −7 d | PBS CONTROL |
|---|---|---|---|---|---|
| Tissue Uptake (% ID/g ± SE) | | | | | |
| Blood (B) | 10.76 ± 1.1 | 14.30 ± .64 | 13.30 ± .69 | 11.75 ± .81 | 3.58 ± .49 |
| Liver (L) | 7.35 ± .67 | 7.52 ± .36 | 7.37 ± .41 | 7.90 ± .62 | 30.04 ± 1.6 |
| Tumor (T) | 21.56 ± 1.0 | 22.77 ± .1.3 | 20.15 ± .61 | 25.13 ± 1.9 | 24.69 ± 2.5 |
| Tissue Ratios (±SE) | | | | | |
| T/L | 3.28 ± .43 | 3.03 ± .10 | 2.78 ± .15 | 3.30 ± .32 | 0.98 ± .18 |
| T/B | 2.23 ± .43 | 1.62 ± .11 | 1.53 ± .06 | 2.20 ± .20 | 9.16 ± .82 |
| L/B | 0.70 ± .05 | 0.53 ± .03 | 0.56 ± .04 | 0.69 ± .06 | 14.3 ± 2.0 |
| Tumor Weight (g ± SE) | 0.65 ± .15 | 0.45 ± .10 | 0.71 ± .12 | 0.63 ± .17 | 0.55 ± .05 |

TABLE IV-continued
EFFECT OF TIMING OF PRETREATMENT ON BIODISTRIBUTION OF
INDACEA IN NUDE MICE BEARING SUBCUTANEOUS LS174T XENOGRAFTS

| Time of Pre-treatment Prior To Indacea | −20 m | −13 h | −48 h | −7 d | PBS CONTROL |
|---|---|---|---|---|---|
| Number of Mice (n) | 7 | 8 | 7 | 7 | 29 |

As seen in Table IV, all MAB pretreated groups demonstrated a significantly lower ($p<0.0005$) liver uptake of Indacea (7.35 to 7.90 % ID/g) compared to the untreated control group (30.04 % ID/g). As previously observed, the level of radioactivity in the blood of the treated animals was significantly higher ($p<0.005$) than that of the PBS control animals. Biodistribution data of the four treated groups shows no significant difference in tissue uptake for blood, liver or tumor among the four groups pretreated with T84.66 MAB and subsequently treated with T84.66 Indacea.

The following example compares the effects of the route of administration of the pretreatment antibody on biodistribution.

EXAMPLE 5

Nude mice were inoculated sc with $1 \times 10^6$ LS174T cells on day 0 and divided into four treatment groups. Two of the groups received single dose injections of T84.66 MAB (0.2 mg) 7 days after administration of tumor cells and thereafter received by Indacea (T84.66) 7 days later. One of these groups received the antibody intravenously (iv) (group A) and the other intraperitoneally (ip) (group C). The other two groups received 0.2 mg T84.66 MAB simultaneously with Indacea on day 14. One of these groups was injected iv (group B) and the other ip (group D). All the animals were euthanized and tissue uptake of the label determined at 48 hours (day 16) after Indacea injection.

The results of these experiments are shown in Table V.

between the T/L, T/B or L/B ratios of these two groups.

A similar comparison between iv and ip administration of the antibody in which the unlabeled MAB was injected simultaneously with the labeled MAB (groups B and D) shows that the only effect on tissue biodistribution is a slightly higher T/L ratio with the ip injection ($p<0.05$).

The Table V results also show that for ip administration, giving the unlabeled MAB 7 days prior to Indacea resulted in a lower liver uptake of label ($p<0.01$), a lower L/B ratio ($p<0.01$) and a higher T/L ratio ($p<0.05$) compared to the simultaneous administration of the unlabeled and labeled MAB. However, in the instance of iv injection, the L/B ratios for pretreatment and simultaneous administration were virtually identical. There was also a small, but significant ($p<0.05$) decrease in tumor uptake with the simultaneous injection.

The specificity of the antibody used for pretreatment was determined in the following example.

EXAMPLE 6

Three experiments were performed to examine the specificity of the MAB used in pretreatment steps. In each experiment, nude mice received $1 \times 10^6$ LS174T tumor cells on day 0 and were divided into 4 groups. Each group received 0.2 mg of either T84.66, T84.12, ZCE025 or PBS ip on day 7. On day 14, the mice were given 2 μg (10 μCi) of either T84.66 Indacea (FIG. 4a), ZCE025 Indacea (FIG. 4b), or T84.12 Indacea FIG. 4c). Imaging and tissue biodistributions were done at 48 hours (day 16). All MAB injections were ip.

Figure 4A:
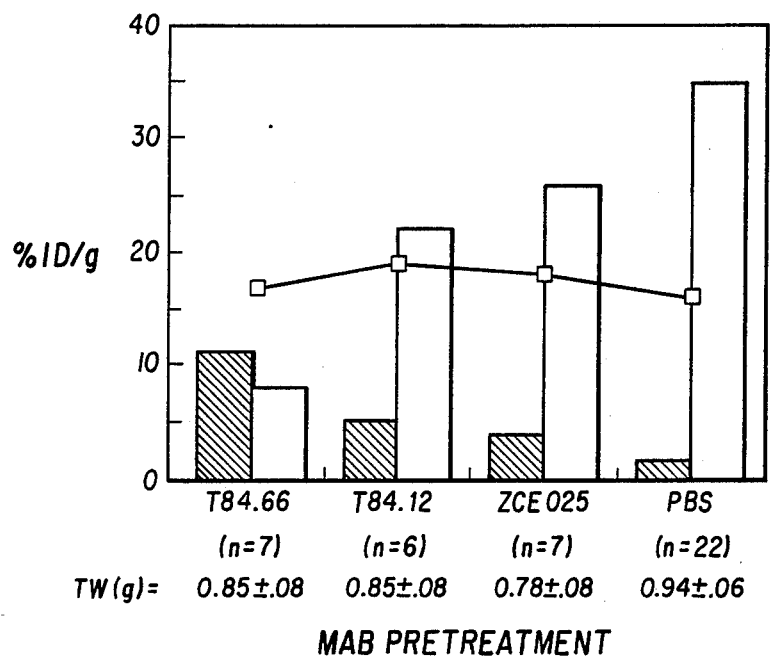
FIG. 4a shows the specificity of the pretreatment effect of three MABs specific for CEA (ZCE025, T84.66 and T84.12) when followed by $^{111}$In-labeled T84.66.
Figure 4B:
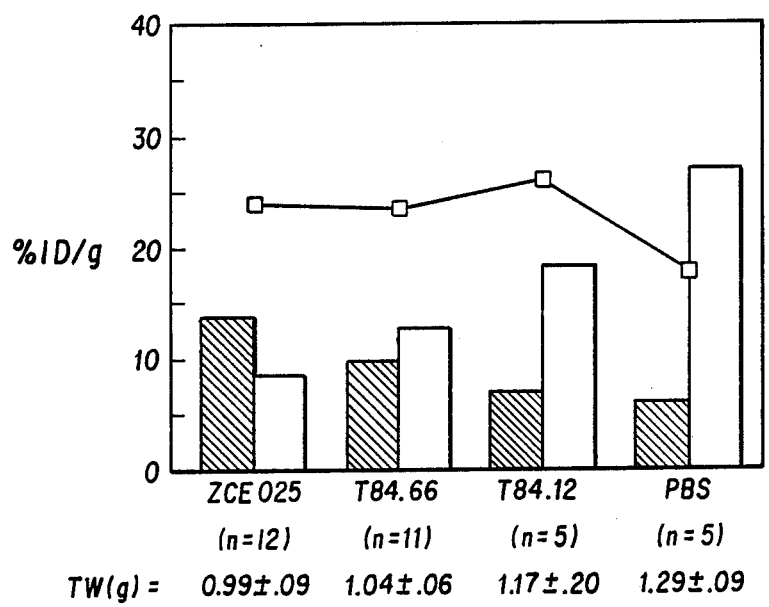
FIG. 4b shows the specificity of the pretreatment effect of three MABs specific for CEA (ZCE025, T84.66 and T84.12) when followed by $^{111}$In-labeled ZCE025.
Figure 4C:
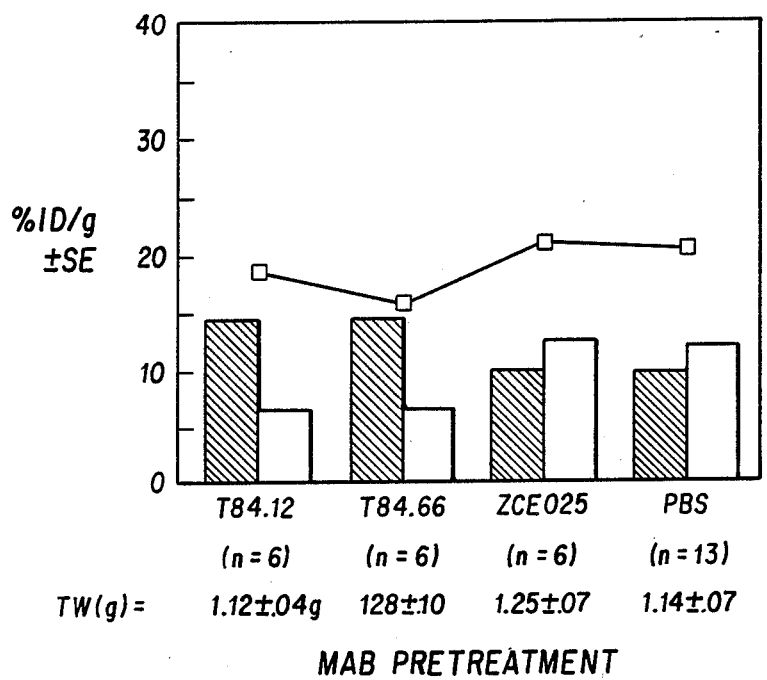
FIG. 4c shows the specificity of the pretreatment effect of three MABs specific for CEA (ZCE 025, T84.66 and T84.12) when followed by $^{111}$In-labeled T84.12.

As seen in FIG. 4a, pretreatment with ZCE025 and T84.12 produced 25.6% and 36.4% decrease in liver TABLE V
EFFECT OF ROUTE OF INJECTION OF PRETREATMENT ON BIODISTRIBUTION
OF INDACEA IN NUDE MICE BEARING SUBCUTANEOUS LS174T XENOGRAFTS

| | Route of MAB Administration | | | |
|---|---|---|---|---|
| | A | B | C | D |
| | Intravenous | | Intraperitoneal | |
| | Time of MAB Administration Prior to Indacea | | | |
| | −7 d | 0 | −7 d | 0 |
| Tissue Uptake (% ID/g ± SE) | | | | |
| Blood (B) | 8.30 ± .73[a] | 9.48 ± .67 | 11.62 ± .71[a] | 10.38 ± .86 |
| Liver (L) | 11.04 ± .98 | 12.39 ± .63 | 9.42 ± .47[b] | 11.18 ± .40[b] |
| Tumor (T) | 19.18 ± .55[c] | 17.53 ± .77[c] | 19.82 ± .58 | 19.30 ± 1.81 |
| Tissue Ratios (±SE) | | | | |
| T/L | 2.07 ± .38 | 1.44 ± .06[d] | 2.14 ± .11[e] | 1.73 ± .15[d,e] |
| T/B | 2.23 ± .33 | 1.95 ± .14 | 1.76 ± .14 | 2.02 ± .23 |
| L/B | 1.36 ± .31 | 1.35 ± .10 | 0.82 ± .05[f] | 1.19 ± .13[f] |
| Tumor Weight (g ± SE) | 0.98 ± .13 | 1.03 ± .07 | 0.95 ± .08 | 0.93 ± .09 |
| Number of Mice (n) | 6 | 14 | 7 | 12 |

[a] = $p < 0.005$
[b,f] = $p < 0.01$
[c,d,e] = $p < 0.05$

As seen above, administration of unlabeled MAB 7 days prior to the labeled MAB either iv (group A) or ip (group C), caused no significant effect on tumor or liver uptake. However, the level of indium-111 in the blood was lower at 48 hours with the iv route of administration ($p<0.005$). There were no significant differences uptake of Indacea respectively, relative to the PBS control. However, pretreatment with T84.66 lowered the level of Indacea in the liver by 76.8%. Concomitant with the decrease in liver radioactivity, was an increased level of radiolabel in the blood. The T/L ratio showed a significant increase from $0.46\pm0.06$ in the nontreated mice to $2.16\pm0.13$ in the mice pretreated with T84.66 MAB ($p<0.0005$). The L/B ratio was lowered from $23.18\pm3.42$ to $0.72\pm0.06$, with T84.66 pretreatment ($p<0.0005$). The tumor uptake (% ID/g) was not affected by the pretreatments.

The above protocol was repeated using ZCE025 Indacea (FIG. 4b) and T84.12 Indacea (FIG. 4c) as the imaging MABs. There was no significant decrease in tumor uptake of the $^{111}$In-MAB with pretreatment at the 0.2 mg level for any of the combinations. For each antibody, the maximum decrease in liver uptake obtained with pretreatment occurred when the animals were treated with the same MAB as that used for imaging. However, for mice receiving T84.12 Indacea or ZCE025 Indacea, pretreatment with T84.66 caused a decrease in liver uptake that was not statistically different from that obtained with T84.12 or ZCE025 pretreatment matched with the Indacea. The reverse was not true, however. Pretreatment with T84.12 or ZCE025 was not as effective as T84.66 when T84.66 Indacea was the imaging agent.

Comparison of the PBS controls for the three $^{111}$In-labeled antibodies (FIGS. 4a, 4b, 4c) shows a noticeable difference in liver uptake. The highest liver uptake was seen with T84.66 Indacea ($34.94\pm1.61$ % ID/g), which was three times that observed with T84.12 Indacea ($11.98\pm0.81$ % ID/g). The average tumor size in these two groups was $0.88\pm0.09$ g and $1.14\pm0.07$ g, respectively, thereby minimizing differences in liver uptake due to differences in tumor mass.

Due to the differences in liver uptake of the three radiolabeled MABs seen in the untreated control animals in Example 5, the antibody affinity of these three antibodies was measured using a solid phase EIA as described by Beatty, J. D., et al., *J. Immunol. Methods* 100:173-179 (1987). The affinity constants of T84.66, ZCE025 and T84.12 so measured are $4.67\times10^{-10}$ (L/M), $6.80\times10^{-9}$ (L/M) and $5.65\times10^{-9}$ (L/M), respectively. With respect to the data in Example 5, T84.66 showed the highest affinity for CEA and was also the only MAB to successfully lower the liver uptake for all three MABs tested. Similarly, $^{111}$In-labeled T84.66 exhibits the highest liver uptake of the label in the absence of pretreatment.

Clearly MAB affinity for the marker substance to be targeted or treated is to be considered when designing a treatment protocol. The above data suggests that a relatively large dose of MAB with a high affinity for a particular marker substance used for pretreatment followed by a labeled lower affinity MAB directed against a different epitope on the marker substance may yield the highest T/L ratios.

Though the examples illustrate the enhanced biodistribution of particular antibodies to a particular marker substance or antigen (CEA), the instant invention is not to be construed to be limited to the exemplified antibody-antigen pairs. Likewise, the timing of pretreatment in cases where labeled and unlabeled antibody are not simultaneously administered is not limited by the above examples. Preferable timing of pretreatment is from about three weeks to about 20 minutes prior to the administration of a labeled antibody.

The antibodies used in the method of this invention may be specific for intracellular, cytoplasmic, or cell surface marker substances. Fragments of antibodies may also be used. These antibodies are preferably monoclonal of mammalian origin and may be synthesized by genetic engineering technology well known in the art, or they may be synthesized in vitro or in vivo utilizing genetic engineering technology. Of particular value are chimeric antibodies comprising murine variable region and human constant region or any other type specific for a given marker substance antibody.

Marker substances may be produced by lesions, or they may simply accumulate in, on, or near lesions. Substances suitable as markers for which antibodies used in accordance with this invention may be specific generally include, but are not limited to oncofetal antigens, tumor antigens, receptors, hormones and enzymes. Examples of such marker substances are human chorionic gonadotropin (HCG) and/or its beta subunit, alpha-fetoprotein (AFP), Ca 19-9, CA125, 132CS, tissue polypeptide antigen, colon-specific antigen-p ($CSA_p$), A 431, TA-4, prostatic acid phosphatase, pancreatic oncofetal antigen, T101, S 100, parathormone, B1.1, TAG72, placental alkaline phosphatase, calcitonin, mammary tumor-associated glycoproteins, galactosyl transferase-II (gt-II), glial fibrillary acidic protein (GFA), tumor angiogenesis factor (TAF), prostatic acid phosphatase, pregnancy $beta_1$-globulin, $beta_2$-microglobulin ovarian cystadenocarcinoma-associated antigen (OCAA), ovarian tumor-specific antigen, common glioma antigen (CGA), cervical cancer antigens, glioembryonic antigen (GEA), common meningioma antigen (CMA), terminal deoxynucleotidyl transferase (TAT), and cytomplasmic melanoma-associated antigens.

Substances which may be used as detectable labels for the antibodies used in the methods of this invention include various isotopes of the transition metals. In general, any transition metal isotope that gives off alpha particles, beta particles, gamma rays, or any other emission that could be used for detection or therapy may be used. These include but are not limited to iodine-131, iodine-123, iodine-126, iodine-133, bromine-66, fluorine-18, indium-111, indium-113m, technetium-99m, gallium-67, gallium-68, ruthenium-95, ruthenium-97, ruthenium-103, ruthenium-105, mercury-197, mercury-203, scandium-47, tellurium-121m, tellurium-122m, tellurium-125m, rhenium-99m, rhenium-101, rhenium-105, thulium-165, thulium-167, thulium-168, thallium-202, and antimony. Magnetic contrast agents such as gadolinium, manganese, and iron, which do not emit particles or rays, possess a property which is identifiable by the agents' ability to resonate at a certain frequency due to magnetic resonance, and as such may also be used as detectable labels.

Substances which may be used as therapeutic labels for the antibodies used in the methods of this invention include various isotopes of the transition metals and chemotherapeutic drugs. These include, but are not limited to yttrium-90, methotrexate, copper-67, indium-194, cobalt, carbon-14, daunomycin, vincristine, 5-fluorouracil, BCNU, nitrogen mustard, vinblasatin, cyclophosphamide, actinomycin D, 6-mercaptopurine, arabinosyl, cytosine, L-asparaginase, adriamycin, cytoxin, busulfan, chlorambucil, thiotepa, melphalan, thioguanine, hydroxyurea, procarbazine, o,p-D,D,D, FUDR, mithramycin, bleomycin, DTIC, CCNU, and cis-platinum.

In addition to a therapeutically effective label, a radioactive or otherwise detectable level may also be attached to or otherwise associated with the subsequently administered antibody.

In another application of the methods of this invention, a human subject is first exposed to a given marker-specific antibody. Subsequently, the same antibody, now labeled with a detectable label and boron-10, is administered to the subject. The lesion is located by detecting the site or sites of labeled subsequently administered antibody accumulation. The lesion with which boron-10-labeled antibody is now associated is later irradiated with a well collimated beam of thermal neutrons. Such irradiation gives rise to cytotoxic particles which have a therapeutic effect. The prior exposure of the human subject to an antibody the same as that which is subsequently administered diminishes uptake of said subsequently administered antibody by the liver and spleen, and thus allows more of the antibody to become associated with marker substance. Inasmuch as marker substance is itself associated with the lesion, antibody accumulation in, on, or near the lesion is increased. In this way, the lesion is more precisely located. The therapeutic agent's cytotoxic effects are also directed more precisely to the lesion and undesired cytotoxicity is minimized.

Instead of whole antibodies, antibody fragments specific for lesion-associated marker substances may be used in accordance with the present invention. Specifically, where it is sought to decrease liver and spleen uptake of antibody fragments and to increase the quantity of antibody fragments which complexes with marker substance, the human subject may be initially exposed to antibody fragments specific for the marker substance. The same broad antibody fragment in labeled form may then be administered to the subject. The prior exposure to the antibody fragment decreases the uptake of the subsequently administered antibody fragment by the subject's liver and spleen. As a corollary of this diminished uptake, more of the antibody fragments is retained by the blood and available for formation of complexes with the lesion-associated marker substance. Such fragments may be associated with detectable and/or therapeutically effective labels as previously described.

What is claimed is:

1. A method for enhancing targeting of a lesion near the liver or spleen of a mammalian subject by administration of a labeled monoclonal antibody specific for a marker substance for said lesion which comprises:

preselecting a combination of unlabeled and detectably labeled lesion marker substance specific monoclonal antibodies, the relative proportion of said unlabeled monoclonal antibodies in said combination being sufficient to substantially clear said lesion marker substance form the bold in circulation in said subject and to provide labeled monoclonal antibody for accumulation is said lesion, and administering said combination of labeled and unlabeled monoclonal antibodies to said mammalian subject in an amount at least sufficient to provide enhanced targeting of said lesion by accumulation of said labeled monoclonal antibody in said lesion.

2. The method of claim 1 wherein said monoclonal antibodies are monoclonal antibodies of mammalian origin.

3. The method of claim 1 wherein said antibody is T84.66 and said label is indium-111.

4. The method of claim 1 wherein said first antibody is T84.66 and said second antibody is ZCE025.

5. The method of claim 1 wherein said antibody is a chimeric antibody of murine/human origin.

6. The method of claim 1 wherein said unlabeled or labeled monoclonal antibodies are administered simultaneously.

7. The method of claim 6 wherein said monoclonal antibody mixture is administered intravenously.

8. The method of claim 1 wherein said lesion-associated marker substance is oncofetal antigen, tumor antigen, a receptor, a hormone, or an enzyme.

9. The method of claim 8 wherein said lesion-associated marker substance is CEA.

10. The method of claim 1 wherein said monoclonal antibodies are fragments of mammalian origin monoclonal antibodies.

11. The method of claim 1 wherein said monoclonal antibodies are chimeric monoclonal antibodies of mammalian origin.

12. The method of claim I wherein said labeled monoclonal antibody comprises a detectable agent.

13. The method of claim 12 wherein said detectable agent is indium-111.

14. The method of claim 1 wherein said unlabeled antibody is administered prior to the administration of said labeled monoclonal antibody.

15. The method of claim 14 wherein said unlabeled monoclonal antibody is administered to said mammal between about 20 minutes and 7 days prior to administration of said labeled antibody.

16. The method of claim 14 wherein said unlabeled monoclonal antibody is administered to said subject in a single dose.

17. The method of claim 14 wherein said unlabeled monoclonal antibody is administered to said subject in multiple doses over time.

* * * * *